United States Patent [19]

Adams et al.

[11] 4,404,417

[45] * Sep. 13, 1983

[54] ISOMERIZATION

[75] Inventors: John R. Adams, Sarnia, Canada; Abraham P. Gelbein, Morristown; Robert Hansen, West Caldwell, both of N.J.; Jimmy Y. Peress, Jamaica, N.Y.; Martin B. Sherwin, Potomac, Md.

[73] Assignee: Polysar International S.A., Switzerland

[*] Notice: The portion of the term of this patent subsequent to Sep. 13, 2000, has been disclaimed.

[21] Appl. No.: 286,643

[22] Filed: Jul. 24, 1981

[51] Int. Cl.³ .............................................. C07C 5/27
[52] U.S. Cl. .................................. 585/671; 252/442; 252/463
[58] Field of Search ................. 585/671; 252/442, 463

[56] References Cited

U.S. PATENT DOCUMENTS

| 3,531,542 | 9/1970 | Myers et al. | 585/671 X |
|---|---|---|---|
| 3,558,733 | 1/1971 | Myers | 585/671 |
| 3,558,734 | 1/1971 | Myers | 585/671 |
| 3,663,453 | 5/1972 | Myers | 585/671 X |
| 3,730,958 | 5/1973 | Myers | 585/671 |
| 3,781,377 | 12/1973 | Myers | 585/671 X |
| 4,038,337 | 7/1977 | Manara et al. | 585/671 |
| 4,225,419 | 9/1980 | Myers | 208/135 |
| 4,229,610 | 10/1980 | Myers et al. | 585/664 |

FOREIGN PATENT DOCUMENTS

| 1065005 | 4/1967 | United Kingdom | 585/671 |
|---|---|---|---|
| 1065006 | 4/1967 | United Kingdom | 585/671 |
| 1065007 | 4/1967 | United Kingdom | 585/671 |
| 1065008 | 4/1967 | United Kingdom | 585/671 |
| 1065010 | 4/1967 | United Kingdom | 585/671 |
| 722886 | 3/1980 | U.S.S.R. | 585/671 |

*Primary Examiner*—Thomas A. Waltz
*Attorney, Agent, or Firm*—Stevens, Davis, Miller & Mosher

[57] ABSTRACT

A process is provided for the skeletal isomerization of straight chain olefins to branched chain olefins by contact at an elevated temperature with a chlorine- or fluorine-containing compound activated alumina catalyst, the alumina having an average particle size of from about $0.5 \times 10^{-3}$ cm to about $160 \times 10^{-3}$ cm and from 3 to 9% of the pore volume being attributable to pores having radii from about 100 to about 10,000 Angstroms.

5 Claims, No Drawings

ISOMERIZATION

FIELD OF THE INVENTION

This invention is directed to a process for the skeletal isomerization of olefins by passage over a catalyst.

DESCRIPTION OF THE PRIOR ART

The quantity of branched chain olefins in olefin mixtures is usually less than the quantity of straight chain olefins in such mixtures. The demand in the petrochemical industry for branched chain olefins is high. U.S. Pat. No. 2,395,274 describes the conversion of aliphatic olefins to isomers of branched structure by passage over a bauxite catalyst at temperatures of 260°–705° C. U.S. Pat. No. 2,943,128 teaches that normal paraffins are isomerized to branched paraffins by contact at 345°–427° C. with a catalyst prepared by precipitating aluminum or zirconium fluoride onto a silica-alumina support, impregnating with a reducible palladium compound and activating by reduction with hydrogen at 400°–525° C. U.S. Pat. No. 3,531,542 shows that a butene feed is isomerized to isobutylene by contact with an alumina catalyst. U.S. Pat. No. 3,558,733 teaches the skeletal isomerization of n-butenes by contact with a catalyst which has been prepared by heating alumina to above 595° C. and exposing it to water while at a temperature of 315°–482° C. U.S. Pat. No. 3,663,453 describes skeletal isomerization of olefins by contact with a zirconium oxide catalyst which has been activated by treatment with a halogen compound. U.S. Pat. No. 3,730,958 teaches skeletal isomerization of olefins by contact with an activated catalyst consisting essentially of alumina promoted with a zirconyl halide and the olefin feed may contain a halogen compound to maintain the catalyst activity. U.S. Pat. 4,038,337 describes the skeletal isomerization of alkenes by contact with a catalyst consisting of alumina which has been treated with defined silicon compounds. U.S. Pat. No. 4,225,419 shows that in the skeletal isomerization of olefins by contact with an alumina catalyst, the catalyst is regenerated by heating at 425° to 705° C. in the presence of oxygen-containing gas and water. U.S. Pat. No. 4,229,610 teaches that mono-olefins are isomerized, while avoiding the occurrence of skeletal isomerization, by contact at 260° to 650° C. with a catalyst comprising alumina containing defined amounts of sodium oxide and silica. British Pat. Nos. 1,065,005 to 1,065,010 describe the skeletal isomerization of butenes to isobutylene by contact with a catalyst consisting of alumina which has been treated with a variety of fluorine-containing compounds. Summary review articles in the literature include the article in Chemical Industry Developments, 1974, Volume 8, Issue No. 7 (July), pages 32–41, and the article in Industrial Engineering Chemistry, Process Des. Dev., 1975, Volume 14, Issue No. 3, pages 227–235.

SUMMARY OF THE INVENTION

The present invention describes a process for the skeletal isomerization of straight chain olefins having 4 to 6 carbon atoms to branched chain olefins by contact at a temperature of about 350° to about 550° C. with a residence time of from about 0.6 to about 2 seconds over a catalyst comprising alumina activated with a chlorine- or fluorine-containing compound characterized in that the catalyst has an average particle size of from about $0.5 \times 10^{-3}$ cm to about $160 \times 10^{-3}$ cm and from about 3% to about 9% of the pore volume of the catalyst as measured by mercury porosimetry is attributable to pores having radii between about 100 and about 10,000 Angstroms.

DESCRIPTION OF THE INVENTION

Straight chain olefins suitable for use in the present invention are the $C_4$, $C_5$ or $C_6$ olefins, such as the butenes, pentenes and hexenes. Mixtures of such olefins may also be used, such as butene-1 and butene-2 or pentene-1 and pentene-2. The olefin may also contain as impurities or as additives butane, pentane or hexane respectively. The feed to the skeletal isomerization catalyst may be a mixture, such as butene-1, butene-2 and butane and may further contain an inert diluent such as nitrogen, carbon dioxide or water and the like. For a feed containing $C_4$ olefin, the product of the isomerization will be isobutylene which is a valuable chemical used for the manufacture of polyisobutylene or butyl rubber or for the manufacture of other chemicals such as methyl tertiary-butyl ether.

The temperature for the skeletal isomerization is from about 350° to about 550° C. A preferred temperature range is from about 400° to about 525° C. and a most preferred temperature range is from about 450° to about 500° C.

The residence time for the skeletal isomerization is from about 0.6 to about 2 seconds, the residence time being defined in the usual manner as the volume of the empty reactor at about 25° C. divided by the volume rate of flow of the feed to the reactor at the conditions of temperature and pressure in the reactor.

The chemical composition of the catalyst for the skeletal isomerization comprises alumina activated with a chlorine- or fluorine-containing compound. A preferred form of the alumina is gamma-alumina although an eta-alumina will also provide the required catalytic effect. The activation of the alumina may be achieved by exposure of the catalyst, at a temperature of about 400° to about 500° C., to a chlorine- or fluorine-containing compound before use for skeletal isomerization. Alternatively, the catalyst may be activated by co-feeding a chlorine- or fluorine-containing compound with the olefin feed. As a preferred alternative, the catalyst may be exposed at about 400° to about 500° C., before use for skeletal isomerization, to a chlorine- or fluorine-containing compound and a chlorine- or fluorine-containing compound is co-fed with the olefin feed to be subjected to skeletal isomerization. Suitable chlorine- or fluorine-containing compounds include chlorine, hydrogen chloride, $C_1$ to $C_4$ alkyl or alkylene chlorides such as methyl chloride, ethyl chloride, ethylene dichloride or t-butyl chloride, hydrogen fluoride and boron trifluoride. Preferred are the chlorine-containing compounds selected from hydrogen chloride, methyl chloride, ethyl chloride and t-butyl chloride. When the chlorine- or fluorine-containing compound is co-fed with the olefin feed, the amount of such compound in the feed is from about 50 to about 3000 ppm, preferably from about 100 to about 1000 ppm and most preferably from about 100 to about 500 ppm, said amounts being in weight and as parts per million (ppm) based on the olefin feed. When the chlorine- or fluorine-containing compound is used to activate the catalyst before skeletal isomerization, the alumina catalyst is activated by exposure, at a temperature of about 400° to about 500° C., to an inert gas such as nitrogen containing from about 0.2 to about 2 volume percent of the chlorine- or fluorine-containing compound for a time of from about 5 to about 45 minutes.

The alumina catalyst generally has a surface area of from about 50 to about 300 m²/g, preferably from about 100 to about 200 m²/g and may have pore volume of from about 0.4 cc/g to about 1 cc/g.

The alumina catalyst has an average particle size of from about $0.5 \times 10^{-3}$ cm to about $160 \times 10^{-3}$ cm and a pore size distribution characterized by having from about 3 to about 9% of the pore volume attributable to pores having radii between about 100 and about 10,000 Angstroms. One method which may be used for determination of the pore size distribution of the alumina catalyst is mercury porosimetry as referred to in the book Experimental Methods in Catalytic Research, edited by R. B. Anderson, published by Academic Press, 1968. At pages 80 and 81 thereof, reference is made to the determination of the volume of pores in various pore size ranges. Mercury porosimetry (also known as the mercury intrusion method) was used for the determination, for the alumina catalysts used in this application, of the pore volume attributable to pores having radii between about 100 and about 10,000 Angstroms. Preferably, the pore volume attributable to pores having radii between about 100 and about 10,000 Angstroms is from about 5% to about 7% of the pore volume. The remaining pores have pore volumes of less than 100 Angstroms. The surface area of the catalysts, as described herein above, was calculated from the mercury porosimetry determination of pore size distribution and pore volume.

Alumina catalysts conforming to the particle size and pore size characteristics as defined herein are commercially available. When the catalyst has a particle size range and a pore size distribution within the aforesaid range, it has been surprisingly found that the skeletal isomerization proceeds under the conditions defined hereinbefore to high conversion and with a high selectivity to the production of the branched chain olefin. It is desirable for subsequent recovery of the branched olefin to operate under conditions such that conversions of straight chain olefin to branched olefin of at least about 30%, preferably up to at least about 35%, are achieved at selectivities of at least about 80% and preferably at least about 85%.

The alumina catalyst may be subjected to a regeneration and reactivation procedure following use for isomerization. As for all isomerization processes, there is a slow but definite build up of carbonaceous material on the catalyst during the course of an isomerization cycle. The reactor containing the catalyst is purged, without changing the temperature, with nitrogen gas to remove any volatile organic compounds, such purging generally being for about 15 to about 30 minutes. The flow of nitrogen is then shut off and air is introduced at a low rate of flow, low enough that the temperature in the reactor does not exceed about 500° to about 550° C. as caused by the exotherm resulting from the combustion of the carbonaceous material on the catalyst. The rate of flow of air is gradually increased and then maintained constant for a further 30 to 60 minutes to ensure removal of essentially all carbonaceous material. The flow of air is discontinued and the reactor is again purged with nitrogen for up to about 15 minutes to ensure removal of oxygen. The regenerated catalyst is then reactivated by providing a flow of an inert gas such as nitrogen containing, for example, about 0.5 volume percent of an alkyl halide such as methyl chloride for a time of from about 10 to about 30 minutes. Following the activation, the alkyl halide flow rate is adjusted to that necessary for the isomerization if being used as a co-feed and the flow of hydrocarbon is initiated to start the isomerization reaction. Alternatively, if the alkyl halide is not being used as co-feed, its flow is terminated and the flow hydrocarbon is initiated.

Preferably, the alumina catalyst contains less than about 0.1 weight percent of sodium and less than about 0.1 weight percent of sulphate ions.

The skeletal isomerization may be carried out at a space velocity of from about 2 gram per hour of olefin feed per gram of catalyst up to about 40 grams per hour of olefin feed per gram of catalyst and preferably at from about 10 to about 20 gram per hour of olefin feed per gram of catalyst. Desirably, the pressure of the straight chain olefin over the catalyst will be from about 0.1 to about 2 atmospheres, preferably from about 0.5 to about 1.5 atmospheres. The linear velocity over the catalyst may be in the range of from about 1 to about 50 cm per second, preferably from about 2 to about 20 cm per second.

EXAMPLE 1

An alumina catalyst was charged to a vertical tubular fixed bed reactor equipped with inlet and outlet lines and maintained at a constant temperature. The reactor volume was about 4.3 cm³ and contained 2.18 g of catalyst. The alumina was in the form of extrudates having an average particle size of $80 \times 10^{-3}$ cm, had a surface area of 244 m²/g, pore volume of 0.71 cc/g and pore size distribution in which 6.5% of the pores had radii between 100 and 10,000 Angstroms. The alumina catalyst was activated by passing nitrogen containing about 0.5 volume percent of methyl chloride over the catalyst at about 475° C., the rate of flow being about 120 cc per minute for about 20 minutes. After activation, the flow of olefin feed was initiated. The olefin feed composition is shown in Table I.

TABLE I

| | |
|---|---|
| n-butane | 4.1 molar percent |
| iso-butane | 16.6 molar percent |
| butene-1 | 48.3 molar percent |
| t-butene-2 | 18.3 molar percent |
| c-butene-2 | 12.8 molar percent |
| methyl chloride | 235–245 ppm |

The reaction was maintained at 472°–473° C., the pressure in the reactor was about 5 mm of mercury above atmospheric and the olefin feed was supplied to the reactor at a rate of from about 5 to about 6.5 grams per hour per gram of catalyst, giving a residence time of from 0.98 to about 1.2 seconds. The reaction was run for 24 hours, with samples of the effluent being periodically analyzed. Analysis of the effluent from the reactor showed that over the 24 hour period, from about 31 to about 39% of the butenes was isomerized with a selectivity to formation of isobutylene of from about 88 to about 95. The results are shown in Table II. Also included in Table II are the values of $K_1$, a calculated measure of catalyst activity which is determined from the equation $$K_1 = \frac{F}{W} \ln \frac{1}{1-X}$$

-continued where $\frac{F}{W}$ is $\frac{\text{grams of feed per hour}}{\text{grams of catalyst}}$ and X is the approach to equilibrium and is defined as $$\frac{\text{conversion of butenes}}{\text{equilibrium conversion of butene}}$$

the equilibrium conversion of butene being calculated from the thermodynamic equilibrium constant for the isomerization of butene-1 to isobutylene at the reaction conditions used. This thermodynamic constant is readily available from a number of textbooks.

TABLE II

| Catalyst Properties | | Example 1 | | | | | Example 2 | | | |
|---|---|---|---|---|---|---|---|---|---|---|
| Surface area | m²/g | 244 | | | | | 244 | | | |
| Pore Volume | cc/g | 0.91 | | | | | 0.91 | | | |
| Pore Size Distribution: | | | | | | | | | | |
| 100 to 10,000 A | % | 6.5 | | | | | 6.5 | | | |
| less than 100 A | % | 93.5 | | | | | 93.5 | | | |
| Reaction Conditions | | | | | | | | | | |
| Reactor Temperature | °C. | 473 | | | | 474 | 474 | 475 | 494 | |
| Inlet Pressure | mmHg | 5 | | | | 6 | 6 | 7 | 7 | |
| Operating Time | Hours | 0.5 | 2.5 | 5.5 | 14.5 | 24.5 | 1 | 3 | 19 | 23 |
| Residence Time | Secs. | 0.995 | 1.0 | 1.0 | 1.11 | 1.0 | 0.39 | 0.39 | 0.4 | 0.4 |
| Grams of feed per hour | | 6.32 | 6.32 | 6.32 | 5.66 | 6.32 | 17.3 | 17.3 | 17.0 | 16.5 |
| Grams of catalyst | | | | | | | | | | |
| Results | | | | | | | | | | |
| Conversion of butene | % | 39.6 | 35 | 33.2 | 33 | 30.9 | 25.7 | 22.7 | 22.9 | 25.3 |
| Selectivity to: | | | | | | | | | | |
| Isobutylene | % | 88 | 93 | 94 | 94 | 95 | 99.5 | 97 | 97 | 97 |
| $C_3$ Olefins | % | 5.3 | 3 | 2.6 | 2.4 | 1.9 | 0 | 1.4 | 1.4 | 1.4 |
| $C_5$ Olefins | % | 5.3 | 3 | 2.5 | 2.3 | 1.9 | 0 | 1.4 | 1.4 | 1.4 |
| Liquids | % | 0.3 | 0.4 | 0.4 | 0.4 | 0.4 | 0.4 | 0 | 0 | 0 |
| $K_1$ | | 11.5 | 8.5 | 7.6 | 6.8 | 6.7 | 13.5 | 11.3 | 11.3 | 13.1 |

EXAMPLE 2

The same catalyst (2.08 g) as used in Example 1 was charged to a reactor having a volume of 4.4 cm³. The catalyst was activated in the same manner as for Example 1. The olefin feed composition is shown in Table III.

TABLE III

| n-butane | 17.2 molar percent |
|---|---|
| iso-butane | 4.2 molar percent |
| butene-1 | 47.2 molar percent |
| t-butene-2 | 18.8 molar percent |
| c-butene-2 | 12.7 molar percent |
| methyl chloride | 240–255 ppm |

The reaction was maintained at 475° C. for the first 20 hours and then at 494° C. for the final 3 hours, the pressure in the reactor was from 6 to 7 mm of mercury above atmospheric and the olefin feed was supplied to the reactor at a rate of from about 16 to about 17 grams per hour per gram of catalyst, giving a residence time of from 0.39 to 0.44 seconds. The reaction was run for 23 hours, with samples of the effluent being periodically analyzed. The results are shown in Table II.

This Example is outside of the scope of the present invention by virtue of the residence time being less than the specified range. Even though the catalyst is fairly active, as shown by the values of $K_1$, the conversion of butenes is below a desirable level.

What is claimed is:

1. A process for the skeletal isomerization of straight chain olefins having 4 to 6 carbon atoms to branched chain olefins by contact at a temperature of about 350° to about 550° C. with a residence time of from about 0.6 to about 2 seconds over a catalyst comprising alumina activated with a chlorine-containing compound characterized in that the alumina catalyst has an average particle size of from about $0.5 \times 10^{-3}$ cm to about $160 \times 10^{-3}$ cm and from about 3 to about 9% of the pore volume of the catalyst as measured by mercury porosimetry is attributable to pores having radii between about 100 and about 10,000 Angstroms, has a surface area of from about 50 to about 300 m²/g and a pore volume of from about 0.4 cc/g to about 1 cc/g, the catalyst is activated by exposure at a temperature of from about 400° to about 500° C. to the chlorine-containing compound and the straight chain olefin feed to the catalyst contains from about 50 to about 3000 ppm by weight based on the olefin of the chlorine-containing compound, said chlorine-containing compound being selected from chlorine, hydrogen chloride and $C_1$ to $C_4$ alkyl or alkylene chlorides.

2. The process of claim 1 wherein the skeletal isomerization temperature is from about 400° to about 525° C.

3. The process of claim 3 wherein the olefin feed is a mixture of $C_4$, $C_5$ or $C_6$ olefins.

4. The process of claim 3 wherein the olefin feed to the catalyst is a mixture of butene-1, butene-2 and butane and contains from about 100 to about 1000 ppm of a chlorine-containing compound selected from methyl chloride, ethyl chloride and t-butyl chloride.

5. The process of claim 4 wherein the catalyst is activated by exposure for a time of from about 5 to about 45 minutes to an inert gas containing from about 0.2 to about 2 volume percent of the chlorine-containing compound.

* * * * *